United States Patent
Kinney et al.

(10) Patent No.: US 7,129,089 B2
(45) Date of Patent: Oct. 31, 2006

(54) ANNEXIN AND P34 PROMOTERS AND USE IN EXPRESSION OF TRANSGENIC GENES IN PLANTS

(75) Inventors: Anthony J. Kinney, Wilmington, DE (US); Zhan-Bin Liu, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 182 days.

(21) Appl. No.: 10/776,889

(22) Filed: Feb. 11, 2004

(65) Prior Publication Data

US 2004/0158052 A1      Aug. 12, 2004

Related U.S. Application Data

(60) Provisional application No. 60/446,833, filed on Feb. 12, 2003.

(51) Int. Cl.
C12H 15/82     (2006.01)
C07H 21/04     (2006.01)
C12N 15/90     (2006.01)
A01H 5/00      (2006.01)

(52) U.S. Cl. .................. 435/468; 435/320.1; 536/24.1; 800/281; 800/287

(58) Field of Classification Search ........ 800/278–289; 435/320.1, 419, 468
See application file for complete search history.

(56) References Cited

U.S. PATENT DOCUMENTS 5,589,583 A     12/1996   Klee et al.
6,177,613 B1     1/2001   Coughlan et al.

FOREIGN PATENT DOCUMENTS

WO     WO 00/18963      4/2000

OTHER PUBLICATIONS

Bobb et al., Nucleic Acids Research, 25:641-647, 1997.*
Clark et al., Plant Physiol., 126:1072-1084, 2001.*
Joaquin Espartero et al., Differential accumulation of S-adenosylmethionine synthetase transcripts in response to salt stress, Plant Mol. Biol., vol. 25:217-227, 1994.
Makoto Matsuoka et al., Tissue-specific light-regulated expression directed by the promoter of a C4 gene, maize pyruvate,orthophosphate dikinase, in a C3 plant, rice, PNAS, vol. 90:9586-9590, Oct. 1993.
Pablo D. Cerdan et al., A 146 bp fragment of the tobacco Lhcb1*2 promoter confers very-low-fluence,low-fluence and high-irradiance responses of phytochrome to a minimal CaMV 35S promoter, Plant Mol. Biol., vol. 33:245-255, 1997.
Rossitza Atanassova et al., Functional analysis of the promoter region of a maize (Zea mays L.) H3 histone gene in transgenic Arabidopsis thaliana, Plant Mol. Biol., vol. 37:275-285, 1998.

Mats Ellerstrom et al., Functional dissection of a napin gene promoter:identification of promoter elements required for embryo and endosperm-specific transcription, Plant Mol. Biol., vol. 32:1019-1027, 1996.
Aine L. Plant et al., Regulation of an *Arabidopsis oleosin* gene promoter in transgenic *Brassica napus*, Plant Mol. Biol., vol. 25:193-205, 1994.
James S. Keddie et al., A seed-specific *Brassica napus* oleosin promoter interacts with a G-box-specific protein and may be bi-directional, Plant Mol. Biol., vol. 24:327-340, 1994.
Zhang-Liang Chen et al., Regulated Expression of Genes Encoding Soybean beta-Conglycinins in Transgenic Plants, Developmental Genetics, vol. 10:112-122, 1989.
Janice W. Edwards et al., Cell-specific expression in transgenic plants reveals nonoverlapping roles for chloroplast and cytosolic glutamine synthetase, PNAS, vol. 87:3459-3463, May 1990.
Thomas Lubberstedt et al., Promoters from Genes for Plastid Proteins Possess Regions with Different Sensitivities toward Red and Blue Light, Plant Phys., vol. 104:997-1006, 1994.
Sheng Luan et al., A Rice cab Gene Promoter Contains Separate cis-Acting Elements That Regulate Expression in Dicot and Monocot Plants, The Plant Cell, vol. 4:971-981, Aug. 1992.
Paul R. Ebert et al., Identification of an essential upstream element in the nopaline synthase promoter by stable and transient assays, PNAS, vol. 84:5747-5749, Aug. 1987.
John C. Walker et al., DNA sequences required for anaerobic expression of the maize alcohol dehydrogenase 1 gene, PNAS, vol. 84:6624-6628, Oct. 1987.
Vadim L. Mett et al., A system for tissue-specific copper-controllable gene expression in transgenic plants: nodule-specific antisense of asparate aminotransferase-P2, Transgenic Research, vol. 5:105-113, 1996.
Richard A. Jefferson et al., GUS fusions: beta-glucuronidase as a sensitive and versatile gene fusion marker in higher plants, The EMBO J., vol. 6(13):3901-3907, 1987.
Fritz Schoffl et al., The function of plant heat shock promoter elements in the regulated expression of chimaeric genes in transgenic tobacco, Mol. Gen. Genet., vol. 217:246-253, 1989.
Elisabeth Truernit et al., The promoter of the *Arabidopsis thaliana* SUC2 sucrose-H+ symporter gene directs expression of beta-glucuronidase to the phloem: Evidence for phloem loading and unloading by SUC2, Planta, vol. 196:564-570, 1995.

(Continued)

*Primary Examiner*—Ashwin Mehta
*Assistant Examiner*—Vinod Kumar

(57) ABSTRACT

A seed specific plant annexin and P34 promoters and subfragments thereof, recombinant expression construct comprising these promoters and their use in driving seed-specific expression of one or more heterologous nucleic acid fragments, such as heterologous nucleic acid fragments encoding reporter constructs or enzymes related to production of fatty acids in plants are described.

10 Claims, 6 Drawing Sheets

OTHER PUBLICATIONS

Figure 6:
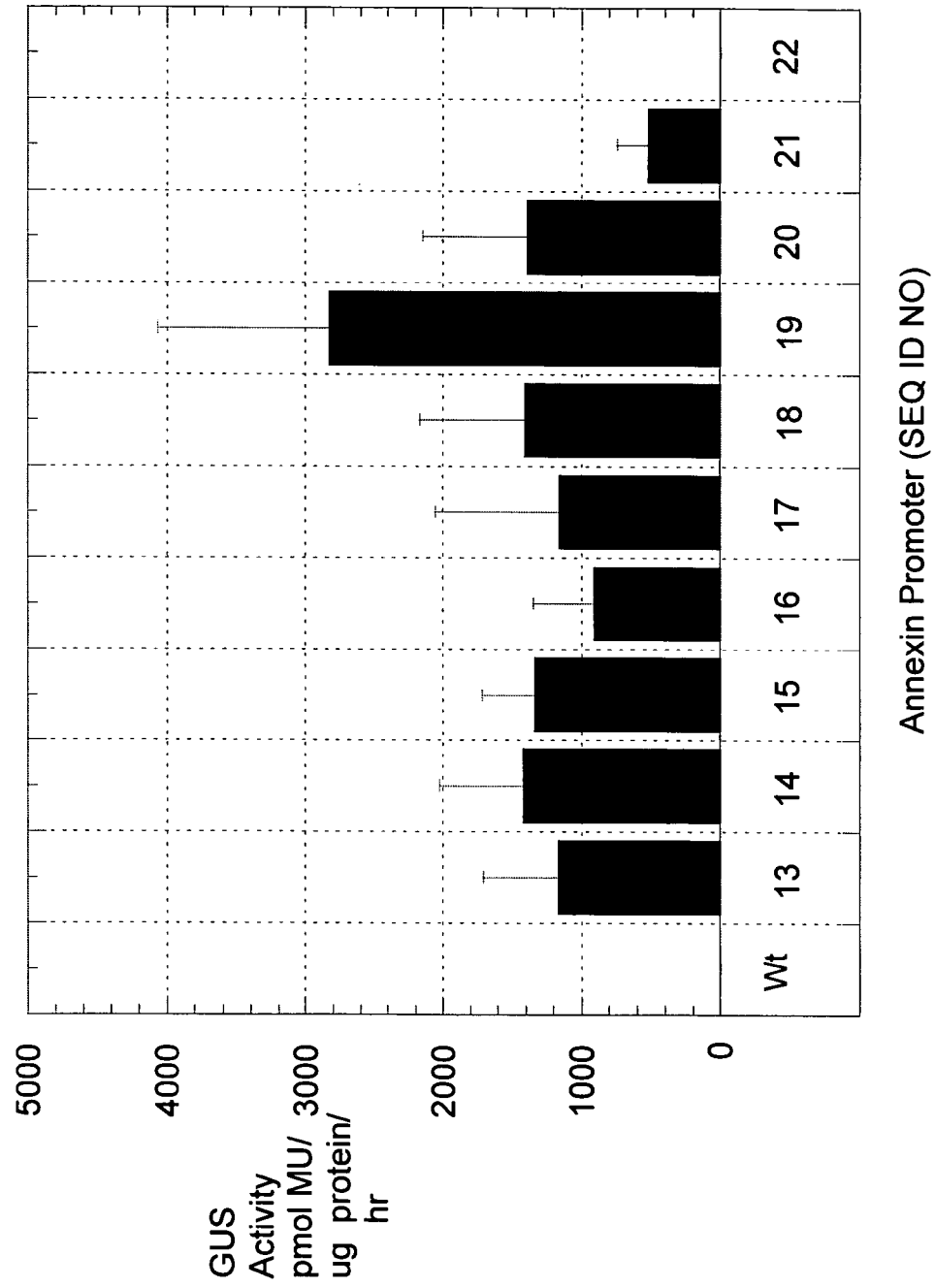

Sonke Holtorf et al., Comparison of different constitutive and inducible promoters for the overexpression of transgenes in *Arabidopsis thaliana*, Plant Mol. Biol., vol. 29:637-646, 1995.

Michael. J. Battraw et al., Histochemical analysis of CaMV 35S promoter-beta-glucuronidase gene expression in transgenic rice plants, Plant Mol. Biol., vol. 15:527-538, 1990.

Michael A. Lawton et al., Expression of a soybean beta-conclycinin gene under the control of the Cauliflower Mosaic Virus 35S and 19S promoters in transformed petunia tissues, Plant Mol. Biol., vol. 9:315-324, 1987.

A. Wilmink et al., Activity of constitutive promoters in various species from the Liliaceae, Plant Mol. Biol., vol. 28:949-955, 1995.

Joan T. Odell et al., Identification of DNA sequences required for activity of the cauliflower mosaic virus 35S promoter, Nature, vol. 313:810-812, 1985.

Mukul Mathur et al., Phytohormonal regulation of S-adenosylmethionine synthetase by gibberellic acid in wheat aleurones, Biochimica at Biophysica Acta., vol. 1137:338-348, 1992.

Thomas Kaiser et al., Promoter elements of the mustard CHS1 gene are sufficient for light regulation in transgenic plants, Plant Mol. Biol., vol. 28:219-229, 1995.

Lourdes Gomez-Gomez et al., Differential Expression of the S-Adenosyl-L-Methionine Synthase Genes during Pea Development, Plant Phys., vol. 117:397-405, 1998.

John M. McDowell et al., The Arabidopsis ACT7 Actin Gene Is Expressed in Rapidly Developing Tissues and Responds to Several External Stimuli, Plant Phys., vol. 111:699-711, 1996.

Tim Ulmasov et al., The Soybean GH2/4 Gene That Encodes a Glutathione S-Transferase Has a Promoter That Is Activiated by a Wide Range of Chemical Agents, Plant Phys., vol. 108:919-927, 1995.

N.-S Yang et al., Maize sucrose synthase-1 promoter directs phloem cell-specific expression of Gus gene in transgenic tobacco plants, PNAS, vol. 87:4144-4148, Jun. 1990.

Vicki L. Chandler et al., Two Regulatory Genes of the Maize Anthocyanin Pathway Are Homologous: Isolation of B Utilizing R Genomic Sequences, Plant Cell, vol. 1:1175-1183, Dec. 1989.

Julie C. Lloyd et al., The chloroplast FBPase gene of wheat: structure and expression of the promoter in photosynthetic and meristematic cells of transgenic tobacco plants, Mol. Gen. Genet., vol. 225:209-216, 1991.

Jorg Stockhaus et al., Correlation of the expression of the nuclear photosynthetic gene ST-LS1 with the presence of chloroplasts, EMBO J., vol. 8(9):2445-2451, 1989.

* cited by examiner

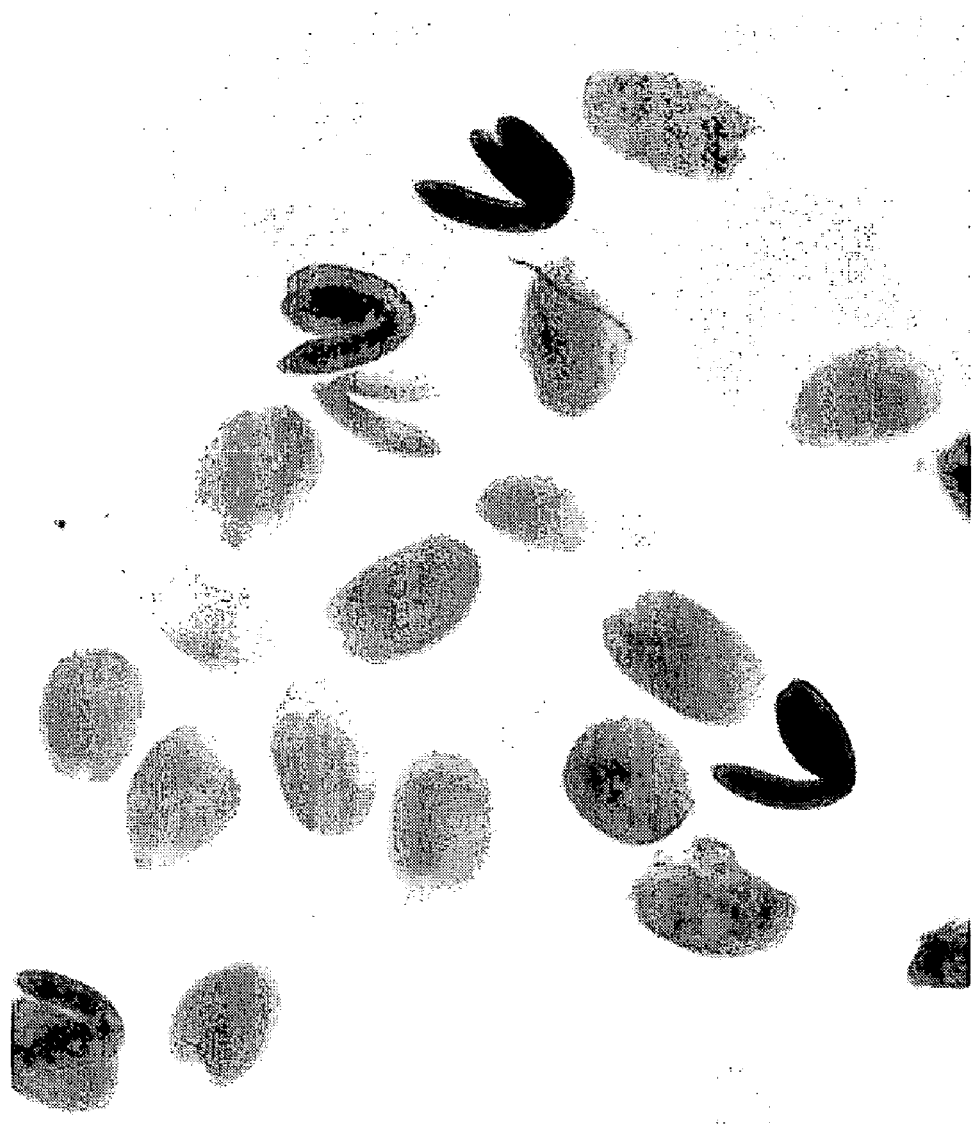
Figure 1: Soybean Annexin Promoter-GUS in Arabidopsis

Figure 2: Soybean P34 Promoter-GUS in Arabidopsis
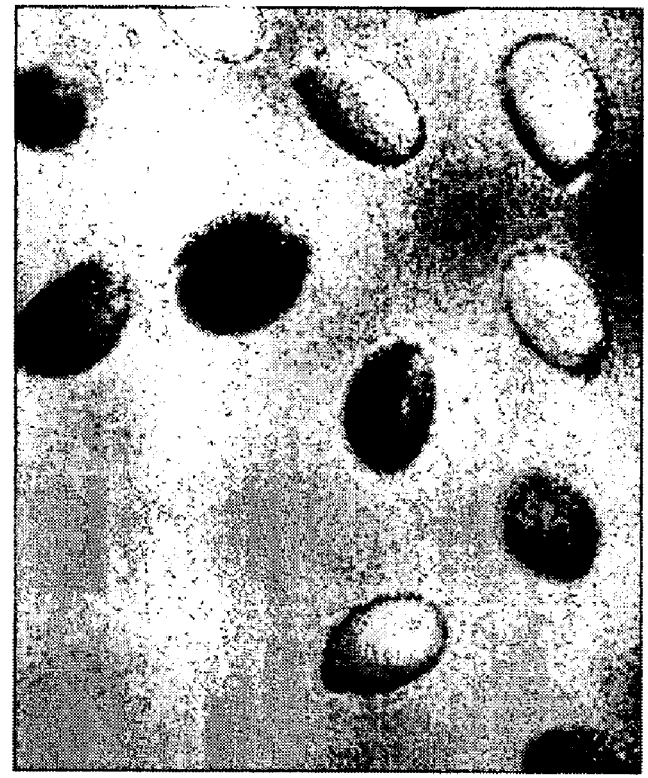
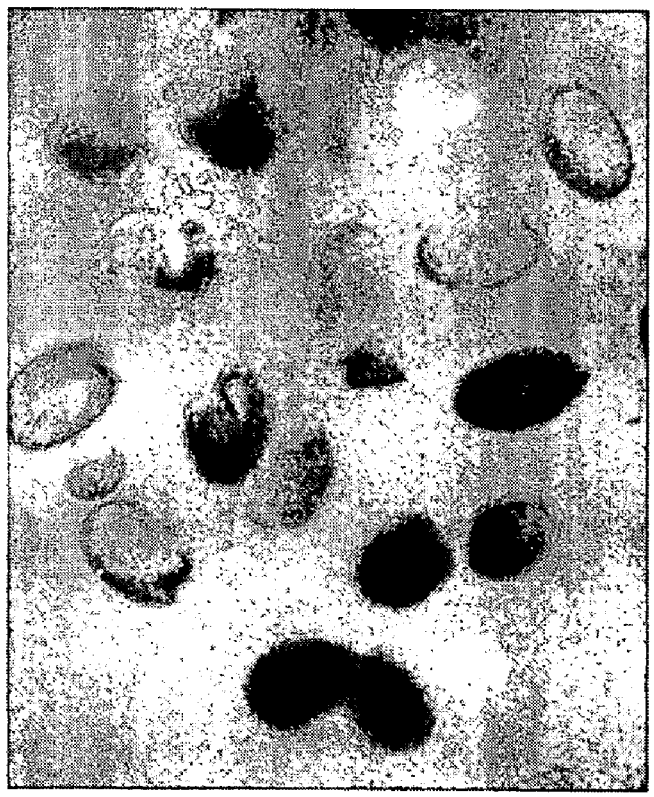

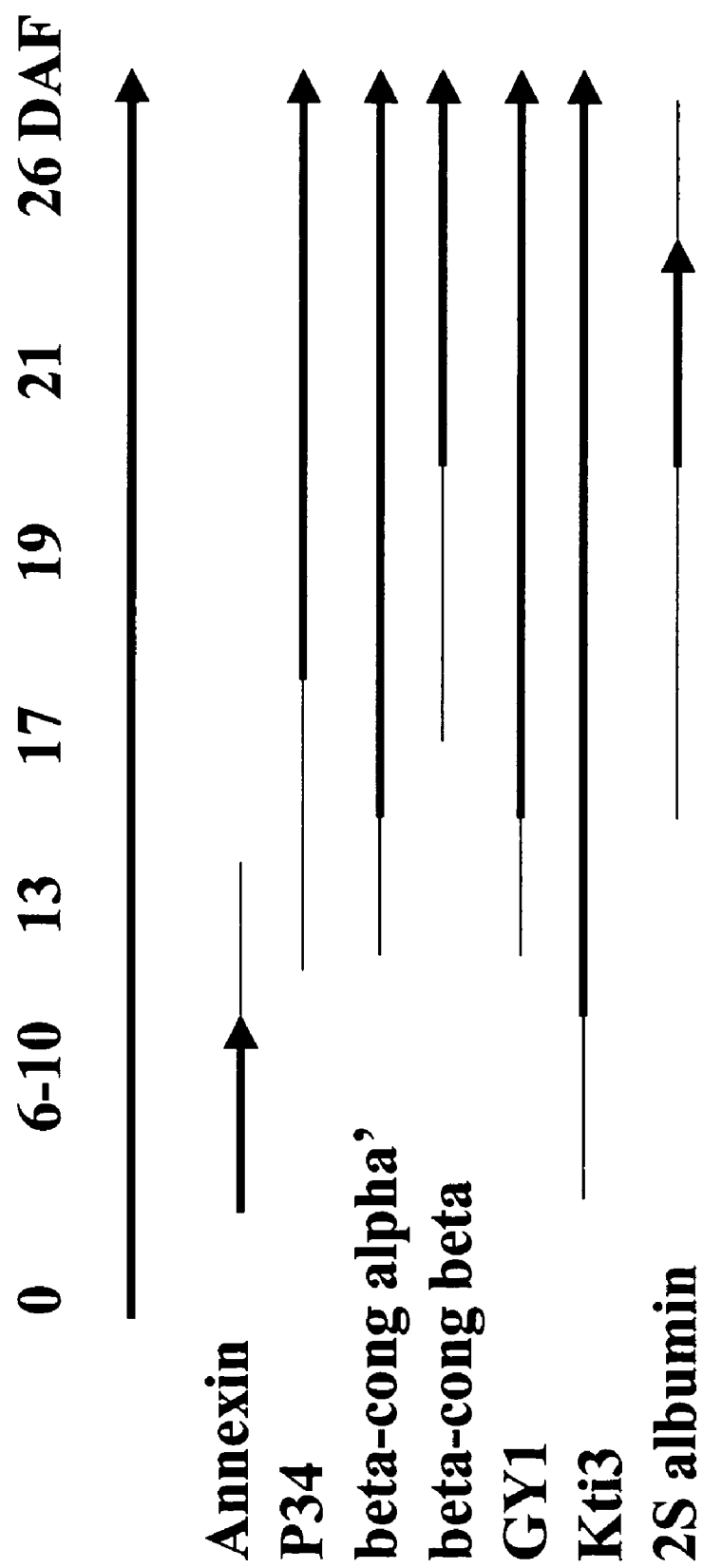
Figure 3: Soybean Seed Promoter Temporal Expression Patterns

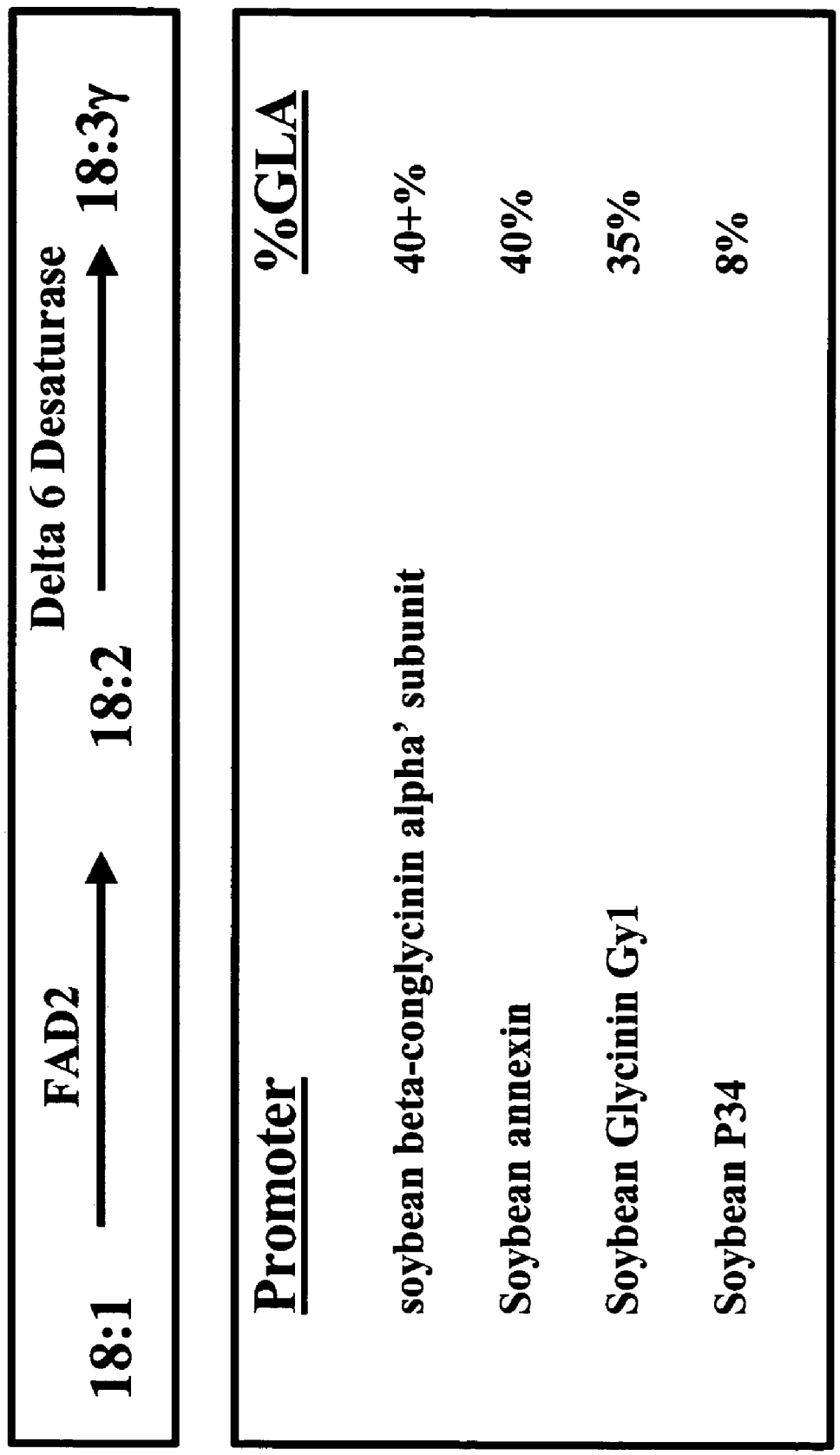
Figure 4: GLA Accumulation in Soybean Somatic Embryos

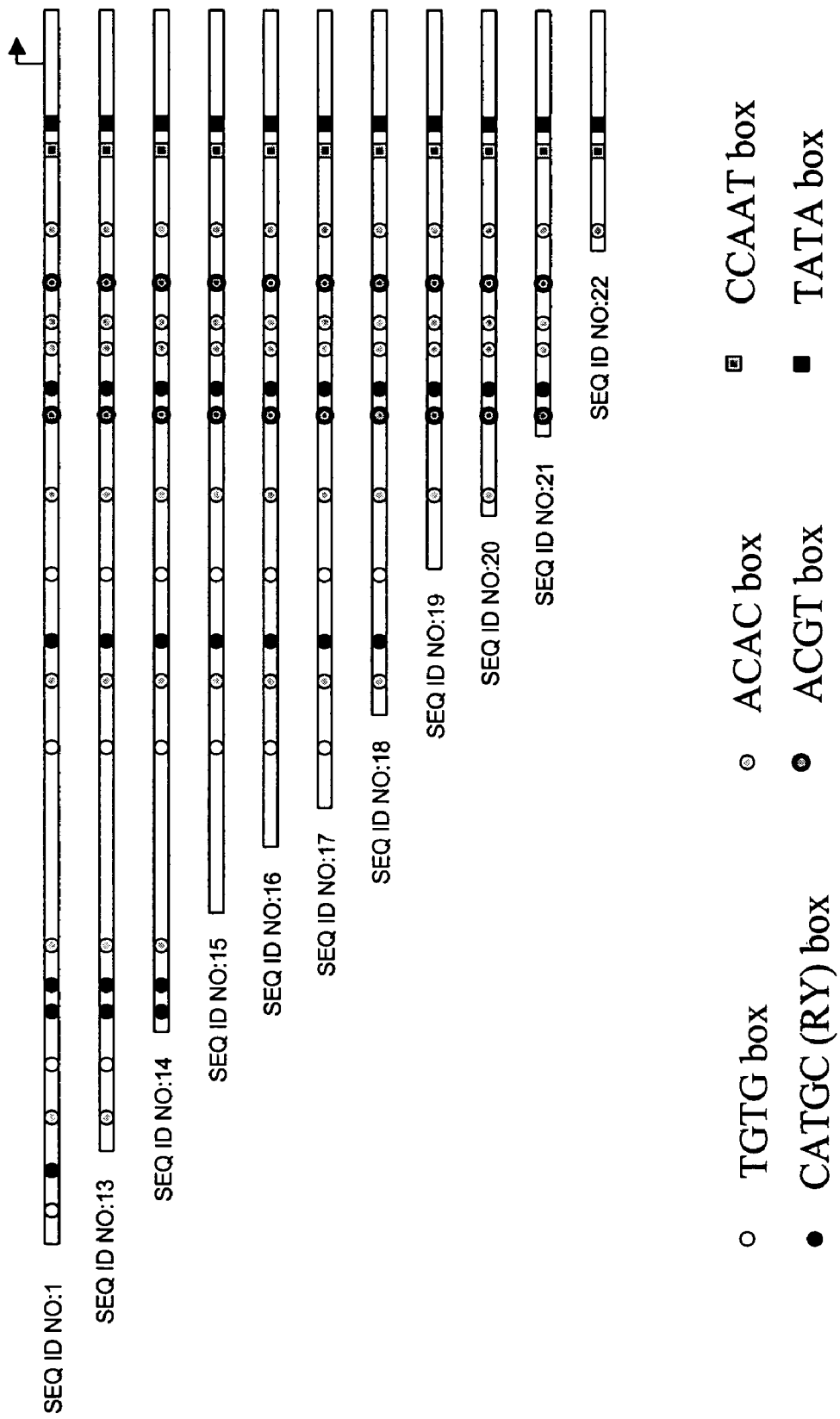
Figure 5: Deletion analyses of soybean Annexin promoter

ANNEXIN AND P34 PROMOTERS AND USE IN EXPRESSION OF TRANSGENIC GENES IN PLANTS

This application claims the benefit of U.S. Provisional Application No. 60/446,833, filed Feb. 12, 2003, the disclosure of which is hereby incorporated by reference in its entirety.

FIELD OF THE INVENTION

This invention relates to a plant promoter, in particular, to annexin and P34 promoters and subfragments thereof and their use in regulating expression of at least one heterologous nucleic acid fragment in plants.

BACKGROUND OF THE INVENTION

Recent advances in plant genetic engineering have opened new doors to engineer plants having improved characteristics or traits, such as, resistance to plant diseases, insect resistance, herbicidal resistance, enhanced stability or shelf-life of the ultimate consumer product obtained from the plants and improvement of the nutritional quality of the edible portions of the plant. Thus, a desired gene (or genes) from a source different than the plant, but engineered to impart different or improved characteristics or qualities, can be incorporated into the plant's genome. This new gene (or genes) can then be expressed in the plant cell to exhibit the desired phenotype such as a new trait or characteristic.

The proper regulatory signals must be present and be in the proper location with respect to the gene in order to obtain expression of the newly inserted gene in the plant cell. These regulatory signals include a promoter region, a 5' non-translated leader sequence and a 3' transcription termination/polyadenylation sequence.

A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce messenger RNA (mRNA) which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cells to cause termination of the RNA transcript and the addition of polyadenylate nucleotides to the 3' end of the RNA.

It has been shown that certain promoters are able to direct RNA synthesis at a higher rate than others. These are called "strong promoters". Certain other promoters have been shown to direct RNA production at higher levels only in particular types of cells or tissues and are often referred to as "tissue specific promoters". In this group, many seed storage protein genes' promoters have been well characterized and widely used, such as the phaseolin gene promoter of *Phaseolus vulgaris,* the helianthinin gene of sunflower, the β-conglycinin gene of soybean (Chen et al., (1989) *Dev. Genet.* 10, 112–122), the napin gene promoter of *Brassica napus* (Ellerstrom et al, (1996) *Plant Mol. Biol.* 32, 1019–1027), the oleosin gene promoters of *Brassica* and *Arabidopsis* (Keddie et al, (1994) *Plant Mol. Biol.* 24, 327–340; Li, (1997) Texas A&M Ph.D. dissertation, pp. 107–128; Plant et al, (1994) *Plant Mol. Biol.* 25, 193–205). Another class of tissue specific promoters is described in, U.S. Pat. No. 5,589,583, issued to Klee et al. on Dec. 31, 1996; these plant promoters are capable of conferring high levels of transcription of chimeric genes in meristematic tissues and/or rapidly dividing cells. In contrast to tissue-specific promoters, "inducible promoters" direct RNA production in response to certain environmental factors, such as heat shock, light, hormones, ion concentrations etc. (Espartero et al, (1994) *Plant Mol. Biol.* 25, 217–227; Gomez-Gomez and Carrasco, (1998) *Plant Physiol.* 117, 397–405; Holtorf et al, (1995) *Plant Mol. Biol.* 29, 637–646; MacDowell et al, (1996) *Plant Physiol.* 111, 699–711; Mathur et al, (1992) *Biochem. Biophys. Acta* 1137, 338–348; Mett et al, (1996) *Transgenic Res.* 5, 105–113; Schoffl et al, (1989) *Mol. Gen. Genet.* 217, 246–253; Ulmasov et al, (1995) *Plant Physiol.* 108, 919–927).

Since the patterns of expression of a chimeric gene (or genes) introduced into a plant are controlled using promoters, there is an ongoing interest in the isolation and identification of novel promoters which are capable of controlling expression of a chimeric gene or (genes). Of particular interest are promoters that express only in the developing seeds. Another desirable feature of a promoter would be an expression pattern that occurs very soon after pollination in the developing seed.

SUMMARY OF THE INVENTION

This invention concerns an isolated nucleic acid fragment comprising a promoter wherein said promoter consists essentially of the nucleotide sequence set forth in SEQ ID NOs:1, 2, 13–22 or said promoter consists essentially of a fragment or subfragment that is substantially similar and functionally equivalent to the nucleotide sequence set forth in SEQ ID NOs:1, 2, 13–22.

In a second embodiment, this invention concerns a chimeric gene comprising at least one heterologous nucleic acid fragment operably linked to the promoter of the invention.

In a third embodiment, this invention concerns plants comprising this chimeric gene and seeds obtained from such plants.

In a fourth embodiment, this invention concerns a method of increasing or decreasing the expression of at least one heterologous nucleic acid fragment in a plant cell which comprises:
  (a) transforming a plant cell with the chimeric gene described above;
  (b) growing fertile mature plants from the transformed plant cell of step (a);
  (c) selecting plants containing the transformed plant cell wherein the expression of the heterologous nucleic acid fragment is increased or decreased.

In a fifth embodiment, this invention concerns an isolated nucleic acid fragment comprising a seed specific plant annexin, or P34, promoter.

BRIEF DESCRIPTION OF THE DRAWINGS AND SEQUENCES

The invention can be more fully understood from the following detailed description, the drawings and the Sequence Descriptions that form a part of this application. The Sequence Descriptions contain the three letter codes for amino acids as defined in 37 C.F.R. §§ 1.821–1.825, which are incorporated herein by reference.

SEQ ID NO:1 is the DNA sequence comprising a 2012 nucleotide soybean annexin promoter.

SEQ ID NO:2 is the DNA sequence comprising a 1408 nucleotide soybean P34 promoter.

SEQ ID NO:3 is an oligonucleotide primer used in the first PCR amplification of the annexin promoter.

SEQ ID NO:4 is an oligonucleotide primer used in the second nested PCR amplification of the annexin promoter.

SEQ ID NO:5 is an oligonucleotide primer used in the first PCR amplification of the P34 promoter.

SEQ ID NO:6 is an oligonucleotide primer used in the second nested PCR amplification of the P34 promoter.

SEQ ID NO:7 is an oligonucleotide primer used in the PCR amplification of the annexin promoter when paired with SEQ ID NO:8 or 11.

SEQ ID NO:8 is an oligonucleotide primer used in the PCR amplification of the annexin promoter when paired with SEQ ID NO:7.

SEQ ID NO:9 is an oligonucleotide primer used in the PCR amplification of the P34 promoter when paired with SEQ ID NO:10 or 12.

SEQ ID NO:10 is an oligonucleotide primer used in the PCR amplification of the P34 promoter when paired with SEQ ID NO:9.

SEQ ID NO:11 is an oligonucleotide primer used in the PCR amplification of the annexin promoter when paired with SEQ ID NO:7.

SEQ ID NO:12 is an oligonucleotide primer used in the PCR amplification of the annexin promoter when paired with SEQ ID NO:9.

SEQ ID NO:13 is a 93.6% truncated form of the annexin promoter (SEQ ID NO:1).

SEQ ID NO:14 is a 85.4% truncated form of the annexin promoter (SEQ ID NO:1).

SEQ ID NO:15 is a 77.2% truncated form of the annexin promoter (SEQ ID NO:1).

SEQ ID NO:16 is a 67.9% truncated form of the annexin promoter (SEQ ID NO:1).

SEQ ID NO:17 is a 57.7% truncated form of the annexin promoter (SEQ ID NO:1).

SEQ ID NO:18 is a 48.1% truncated form of the annexin promoter (SEQ ID NO:1).

SEQ ID NO:19 is a 38.3% truncated form of the annexin promoter (SEQ ID NO:1).

SEQ ID NO:20 is a 29.0% truncated form of the annexin promoter (SEQ ID NO:1).

SEQ ID NO:21 is a 21.2% truncated form of the annexin promoter (SEQ ID NO:1).

SEQ ID NO:22 is a 8.6% truncated form of the annexin promoter (SEQ ID NO:1).

FIG. 1. Soybean Annexin Promoter-GUS Expression in *Arabidopsis*. The dark developing seeds are staining blue due to GUS specific expression in the seeds. This demonstrates that the annexin promoter is capable of directing seed specific expression of a reporter construct. Untransformed seeds are not blue and show up as pale seeds.

FIG. 2. Soybean P34 Promoter-GUS Expression in *Arabidopsis*. As in FIG. 1 the blue staining seeds are transformed with the P34 promoter-GUS construct and shows that P34 is capable of directing seed-specific expression.

FIG. 3. Soybean Seed Promoter Temporal Expression Patterns. Annexin, P34, beta-conglycinin beta subunit, beta-conglycinin alpha' subunit, glycinin, Kunitz trypsin inhibitor, and 2S albumin promoter expression patterns are shown on a timeline of soybean seed development. The times are "days after fertilization" (DAF). The annexin promoter is the earliest known seed specific promoter.

FIG. 4. GLA Accumulation in Soybean Somatic Embryos. The expression of delta-6 desaturase in soybean seeds allows for the accumulation of gamma-linolenic acid (GLA, not normally found in soybean seeds). Expression of delta-6 desaturase by the seed specifc promoters from beta-conglycinin alpha' subunit, annexin, glycinin, and P34 are all capable of generating GLA in transgenic soybeans. The levels of GLA produced by annexin is comparable to levels obtained by the strong beta-conglycinin and glycinin promoters.

FIG. 5. Deletion Analysis of the Soybean Annexin Promoter. The full-length soybean annexin promoter (SEQ ID NO:1) was truncated to form deletion fragments that are tested for promoter activity (SEQ ID NOs:13–22). The regulatory elements discussed in Example 3 are shown.

FIG. 6. Promoter Strength Assays. The full-length and truncated promoters shown in FIG. 5 were fused to a GUS reporter and transformed into *Arabidopsis*. Seeds from *Arabidopsis* transformants were assayed for GUS activity to assess the relative strengths of the various promoters. The results are shown with the standard deviations from the assays.

DETAILED DESCRIPTION OF THE INVENTION

All patents, patent applications, and publications cited herein are incorporated by reference in their entirety.

In the context of this disclosure, a number of terms shall be utilized.

As used herein, an "isolated nucleic acid fragment" is a polymer of ribonucleotides (RNA) or deoxyribonucleotides (DNA) that is single- or double-stranded, optionally containing synthetic, non-natural or altered nucleotide bases. An isolated nucleic acid fragment in the form of DNA may be comprised of one or more segments of cDNA, genomic DNA or synthetic DNA.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 80% to 100%.

Sequence alignments and percent similarity calculations may be determined using the Megalign program of the LASARGENE bioinformatics computing suite (DNASTAR Inc., Madison, Wis.). Multiple alignment of the sequences are performed using the Clustal method of alignment (Higgins and Sharp (1989) *CABIOS*. 5:151–153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4. A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F., et al., (1993) *J. Mol. Biol.* 215:403–410) and Gapped Blast (Altschul, S. F. et al., (1997) *Nucleic Acids Res.* 25:3389–3402).

"Desaturase" is a polypeptide which can desaturate one or more fatty acids to produce a mono- or poly-unsaturated fatty acid or precursor which is of interest.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant DNA construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

A "heterologous nucleic acid fragment" refers to a nucleic acid fragment comprising a nucleic acid sequence that is different from the nucleic acid sequence comprising the plant promoter of the invention.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (1989, *Biochemistry of Plants* 15:1–82). It is further recognized that since in most cases the exact boundaries of regulatory sequences have not been completely defined, DNA fragments of some variation may have identical promoter activity. An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

Among the most commonly used promoters are the nopaline synthase (NOS) promoter (Ebert et al. (1987) *Proc. Natl. Acad. Sci. U.S.A.* 84:5745–5749), the octapine synthase (OCS) promoter, caulimovirus promoters such as the cauliflower mosaic virus (CaMV) 19S promoter (Lawton et al. (1987) *Plant Mol. Biol.* 9:315–324), the CaMV 35S promoter (Odell et al. (1985) *Nature* 313:810–812), and the figwort mosaic virus 35S promoter, the light inducible promoter from the small subunit of rubisco, the Adh promoter (Walker et al. (1987) *Proc. Natl. Acad. Sci. U.S.A.* 84:6624–66280, the sucrose synthase promoter (Yang et al. (1990) *Proc. Natl. Acad. Sci. U.S.A.* 87:4144–4148), the R gene complex promoter (Chandler et al. (1989) *Plant Cell* 1:1175–1183), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al. (1982) *Cell* 29:1015–1026). A plethora of promoters is described in WO 00/18963, published on Apr. 6, 2000, the disclosure of which is hereby incorporated by reference.

Examples of a seed-specific promoter include, but are not limited to, the promoter for β-conglycinin (Chen et al. (1989) *Dev. Genet.* 10: 112–122), the napin promoter, and the phaseolin promoter. Other tissue-specific promoters that may be used to accomplish the invention include, but are not limited to, the chloroplast glutamine synthase (GS2) promoter (Edwards et al. (1990) *Proc. Natl. Acad. Sci. U.S.A.* 87:3459–3463), the chloroplast fructose-1,6-biophosphatase promoter (Lloyd et al. (1991) *Mol. Gen. Genet.* 225:209–2216), the nuclear photosynthetic (ST-LS1) promoter (Stockhaus et al. (1989) *EMBO J.* 8:2445–2451), the serine/threonine kinase (PAL) promoter, the glucoamylase promoter, the promoters for the Cab genes (cab6, cab-1, and cab-1R, Yamamoto et al. (1994) *Plant Cell Physiol.* 35:773–778; Fejes et al. (1990) *Plant Mol Biol.* 15:921–932; Lubberstedt et al. (1994) *Plant Physiol.* 104:997–1006; Luan et al. (1992) *Plant Cell* 4:971–981), the pyruvate orthophosphate dikanase promoter (Matsuoka et al. (1993) *Proc. Natl. Acad. Sci. U.S.A.* 90:9586–9590), the LhcB promoter (Cerdan et al. (1997) *Plant Mol. Biol.* 33:245–255), the PsbP promoter (Kretsch et al. (1995) *Plant Mol. Biol.* 28:219–229), the SUC2 sucrose H+ symporter promoter (Truernit et al. (1995) Planta 196:564–570), and the promoters for the thylakoid membrane genes (psaD, psaF, psaE, PC, FNR, atpC, atpD), etc.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

"Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065. The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the production of a functional end-product e.g., a mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at post-transcriptional level.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) *Plant J.* 16:651–659; and Gura (2000) *Nature* 404:804–808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999 and PCT Publication WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Neither of these co-suppressing phenomena have been elucidated mechanistically at the molecular level, although genetic evidence has been obtained that may lead to the identification of potential components (Elmayan et al. (1998) *Plant Cell* 10:1747–1757).

"Altered expression" refers to the production of gene product(s) in transgenic organisms in amounts or proportions that differ significantly from the amount of the gene product(s) produced by the corresponding wild-type organisms.

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of corn cell transformation is use of particle-accelerated or "gene gun" transformation technology (Klein et al. (1987) *Nature (London)* 327:70–73; U.S. Pat. No. 4,945,050).

Standard recombinant DNA and molecular cloning techniques used herein are well known in the art and are described more fully in Sambrook, J., Fritsch, E. F. and Maniatis, T., *Molecular Cloning: A Laboratory Manual;* Cold Spring Harbor Laboratory Press, Cold Spring Harbor, 1989 (hereinafter "Sambrook et al., 1989") or Ausubel, F. M., Brent, R., Kingston, R. E., Moore, D. D., Seidman, J. G., Smith, J. A. and Struhl, K. (eds.), *Current Protocols in Molecular Biology,* John Wiley and Sons, New York, 1990 (hereinafter "Ausubel et al., 1990").

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

An "expression construct" is a plasmid vector or a subfragment thereof comprising the instant chimeric gene. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Although the annexin, or P34, polypeptides are known to be present in seeds, the promoters responsible for expression of these polypeptides, and the developmental timing of these promoters, have not been previously described. It was not possible to predict, before the studies reported herein, whether any annexin, or P34, gene was controlled by a seed-specific promoter. It is demonstrated herein that seed-specific annexin, or P34, promoters do, in fact, exist in plants, and that such promoters can be readily isolated and used by one skilled in the art.

This invention concerns an isolated nucleic acid fragment comprising a seed-specific plant annexin, or P34, promoter. This invention also concerns an isolated nucleic acid fragment comprising a promoter wherein said promoter consists essentially of the nucleotide sequence set forth in SEQ ID NOs:1 or 2, or said promoter consists essentially of a fragment or subfragment that is substantially similar and functionally equivalent to the nucleotide sequence set forth in SEQ ID NOs:1 or 2. A nucleic acid fragment that is functionally equivalent to the instant annexin, or P34, promoter is any nucleic acid fragment that is capable of controlling the expression of a coding sequence or functional RNA in a similar manner to the annexin, or P34, promoter. The expression patterns of annexin, or P34, promoters are set forth in Examples 2 and 3.

The promoter activity of the soybean genomic DNA fragment upstream of the annexin, or P34, protein coding sequence was assessed by linking the fragment to a reporter gene, the *E. coli* β-glucuronidase gene (GUS) (Jefferson (1987) Plant Mol. Biol. Rep. 5:387–405), transforming the annexin, or P34, promoter::GUS expression cassette into Arabidopsis, and analyzing GUS expression in various cell types of the transgenic plants (see Example 2). GUS expression was restricted to the seeds although all parts of the transgenic plants were analyzed. These results indicated that the nucleic acid fragment contained seed specific promoters.

It is clear from the disclosure set forth herein that one of ordinary skill in the art could readily isolate a plant annexin, or P34, promoter from any plant by performing the following procedure:

1) obtaining an annexin, or P34, cDNA from a desired plant by any of a variety of methods well known to those skilled in the art including, but not limited to, (a) random sequencing of ESTs from a cDNA library and characterizing the ESTs via a BLAST search as described above; or (b) hybridizing a cDNA library to a known plant annexin, or P34, cDNA; or (c) PCR amplification using oligonucleotide primers designed from known annexin, or P34, cDNAs;

2) fragmenting genomic DNA with a restriction enzyme leaving blunt-ends and annealing adaptors onto the ends of the fragments. Using primers specific for the 5' end of the annexin or P34 transcript, and primers specific for the adaptors, to amplify the promoter region in a polymerase chain reaction.

3) operably linking the nucleic acid fragment containing the annexin, or P34, promoter sequence to a suitable reporter gene;there are a variety of reporter genes that are well known to those skilled in the art, including the bacterial GUS gene, the firefly luciferase gene, and the green fluorescent protein gene; any gene for which an easy an reliable assay is available can serve as the reporter gene 4) transforming a chimeric annexin, or P34, promoter:: reporter gene expression cassette into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, cocoa and the monocots, corn, wheat, rice, barley and palm. The terms "oilseed rape" and "oilseed Brassica" are used interchangeably herein.

5) testing for expression of a annexin, or P34, promoter in various cell types of transgenic plant tissues, e.g., leaves, roots, flowers, seeds, transformed with the chimeric annexin, or P34, promoter::reporter gene expression cassette by assaying for expression of the reporter gene product. A strong seed-specific annexin, or P34, promoter will produce high level expression of the reporter in seeds without producing detectable expression in other plant tissues.

In another aspect, this invention concerns a recombinant DNA construct comprising at least one heterologous nucleic acid fragment operably linked to any promoter, or combination of promoter elements, of the present invention. Recombinant DNA constructs can be constructed by operably linking the nucleic acid fragment of the invention, i.e., any one annexin, or P34, promoter or a fragment or a subfragment that is substantially similar and functionally equivalent to any portion of the nucleotide sequence set forth in SEQ ID NOs:1, 2, or 13–22, to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

Plasmid vectors comprising the instant recombinant DNA constructs can then be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of *Agrobacterium tumefaciens*, and obtaining transgenic plants have been published, among others, for cotton (U.S. Pat. Nos. 5,004,863, 5,159,135); soybean (U.S. Pat. Nos. 5,569, 834, 5,416,011); Brassica (U.S. Pat. No. 5,463,174); peanut (Cheng et al. (1996) *Plant Cell Rep.* 15:653–657, McKently et al. (1995) *Plant Cell Rep.* 14:699–703); papaya (Ling, K. et al. (1991) Bio/technology 9:752–758); and pea (Grant et al. (1995) Plant *Cell Rep.* 15:254–258). For a review of other commonly used methods of plant transformation see Newell, C. A. (2000) *Mol. Biotechnol.* 16:53–65. One of these methods of transformation uses *Agrobacterium rhizogenes* (Tepfler, M. and Casse-Delbart, F. (1987) *Microbiol. Sci.* 4:24–28). Transformation of soybeans using direct delivery of DNA has been published using PEG fusion (PCT publication WO 92/17598), electroporation (Chowrira, G. M. et al. (1995) *Mol. Biotechnol.* 3:17–23; Christou, P. et al. (1987) *Proc. Natl. Acad. Sci. U.S.A.* 84:3962–3966), microinjection, or particle bombardment (McCabe, D. E. et. al. (1988) *BiolTechnology* 6:923; Christou et al. (1988) *Plant Physiol.* 87:671–674).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In.: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook et al. (1989) Molecular Cloning: A Laboratory Manual, Cold Spring Harbor Press; Maliga et al. (1995) Methods in Plant Molecular Biology, Cold Spring Harbor Press; Birren et al. (1998) Genome Analysis: Detecting Genes, 1, Cold Spring Harbor, N.Y.; Birren et al. (1998) Genome Analysis: Analyzing DNA, 2, Cold Spring Harbor, N.Y.; Plant Molecular Biology: A Laboratory Manual, eds. Clark, Springer, N.Y. (1997)).

The bacterial GUS gene can be successfully expressed in *Arabidopsis* embryos (see FIGS. 1 and 2). Furthermore, a gene encoding delta-6 desaturase from *M. alpina* also successfully expressed by this promoter in transgenic soybeans, as depicted in FIG. 4. This further validates the application of the annexin, or P34, promoter of the invention in plant genetic engineering practice.

The skilled artisan will also recognize that different independent transformation events will result in different levels and patterns of expression of the chimeric genes (Jones et al., (1985) *EMBO J.* 4:2411–2418; De Almeida et al., (1989) *Mol. Gen. Genetics* 218:78–86). Thus, multiple events must be screened in order to obtain lines displaying the desired expression level and pattern. Such screening may be accomplished by northern analysis of mRNA expression, western analysis of protein expression, or phenotypic analysis. Also of interest are seeds obtained from transformed plants displaying the desired expression profile.

The level of activity of the annexin, or P34, promoter is comparable to that of many known strong promoters, such as the CaMV 35S promoter (Atanassova et al., (1998) *Plant Mol. Biol.* 37:275–285; Battraw and Hall, (1990) *Plant Mol. Biol.* 15:527–538; Holtorf et al., (1995) *Plant Mol. Biol.* 29:637–646; Jefferson et al., (1987) *EMBO J.* 6:3901–3907; Wilmink et al., (1995) *Plant Mol. Biol.* 28:949–955), the Arabidopsis oleosin promoters (Plant et al., (1994) Plant Mol. Biol. 25:193–205; Li, (1997) Texas A&M University Ph.D. dissertation, pp. 107–128), the Arabidopsis ubiquitin extension protein promoters (Callis et al., 1990), a tomato ubiquitin gene promoter (Rollfinke et al., 1998), a soybean heat shock protein promoter (Schoffl et al., 1989), and a maize H3 histone gene promoter (Atanassova et al., 1998).

Expression of chimeric genes in most plant cell makes the annexin, or P34, promoter of the instant invention especially useful when seed specific expression of a target heterologous nucleic acid fragment is required. Another useful feature of the annexin promoter is its expression profile in developing seeds. The annexin promoter of the invention is most active in developing seeds at early stages (within 10 days after pollination) and is largely quiescent in later stages (see FIG. 3). The expression profile of the claimed annexin promoter is different from that of many seed-specific promoters, e.g., seed storage protein promoters, which often provide highest activity in later stages of development (Chen et al., (1989) Dev. Genet. 10:112–122; Ellerstrom et al., (1996) Plant Mol. Biol. 32:1019–1027; Keddie et al., (1994) Plant Mol. Biol. 24:327–340; Plant et al., (1994) Plant Mol. Biol. 25:193–205; Li, (1997) Texas A&M University Ph.D. dissertation, pp. 107–128). The P34 promoter has a more conventional expression profile but remains distinct from other known seed specific promoters (see FIG. 3). Thus, the annexin, or P34, promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Methods of isolating seed oils are well known in the art (Young et al, Processing of Fats and Oils, in "The Lipid Handbook" (Gunstone et al eds.) Chapter 5, pp 253–257; London, Chapman & Hall, 1994).

Another general application of the annexin, or P34, promoter of the invention is to construct chimeric genes that can be used to reduce expression of at least one heterologous nucleic acid fragment in a plant cell. To accomplish this a chimeric gene designed for cosuppression of a heterologous nucleic acid fragment can be constructed by linking the fragment to the annexin, or P34, promoter of the present invention. (See U.S. Pat. No. 5,231,020, and PCT Publication WO 99/53050 published on Oct. 21, 1999, PCT Publication WO 02/00904 published on Jan. 3, 2002, and PCT Publication WO 98/36083 published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the annexin, or P34, promoter of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of increasing or decreasing the expression of at least one heterologous nucleic acid fragment in a plant cell which comprises:

(a) transforming a plant cell with the chimeric genes described herein;

(b) growing fertile mature plants from the transformed plant cell of step (a);

(c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

EXAMPLES

The present invention is further defined in the following Examples, in which parts and percentages are by weight and degrees are Celsius, unless otherwise stated. Techniques in molecular biology were typically performed as described in Ausubel, F. M., et al., (1990, Current Protocols in Molecular Biology, John Wiley and Sons, New York) or Sambrook, J. et al., (1989, Molecular cloning—A Laboratory Manual, $2^{nd}$ ed. Cold Spring Harbor Laboratory Press, Cold Spring Harbor, N.Y.). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Isolation of Soybean Annexin and P34 Promoters

The soybean annexin and P34 promoters were isolated using a polymerase chain reaction (PCR) based approach. Soybean genomic DNA was digested to completion with a DNA restriction enzyme that generates blunt ends (DraI, EcoRV, PvuII, or StuI, for example) according to standard protocols. The Universal GenomeWalker™ system from Clonetech™ (user manual PT3042–1) was used to ligate adaptors to the ends of the genomic DNA fragments. Nested primers are also supplied that are specific for the adaptor sequence (AP1 and AP2, for the first and second adaptor primer respectively). Two gene specific primers (GSP1 and GSP2) were designed for the soybean annexin gene based on the 5' coding sequences in annexin cDNA in DuPont EST database. The oligonucleotide sequences of the GSP1 and GSP2 primers have the sequences shown below (SEQ ID NO:3 and 4).

```
SEQ ID NO: 3    5'-GCCCCCCATCCTTTGAAAGCCTGT-3'

SEQ ID NO: 4    5'-CGCGGATCCGAGAGCCTCAGCATCTTG

AGCAGAA-3'
```

The underlined bases are the recognition site for the restriction enzyme BamH I. The AP2 primer from the GenomeWalker™ kit contains a Sal I restriction site.

The AP1 and the GSP1 primers were used in the first round PCR using each of the adaptor ligated genomic DNA populations (DraI, EcoRV, PvuII, or StuI) under conditions defined in the GenomeWalker™ protocol. Cycle conditions were 94° C. for 4 minutes; 94° C. for 2 second and 72° C.

for 3 min, 7 cycles; 94° C. for 2 second and 67° C. for 3 minutes, 32 cycles; 67° C. for 4 minutes. The products from each of the first run PCRs were diluted 50-fold. One microliter from each of the diluted products was used as templates for the second PCR with the AP2 and GSP2 as primers. Cycle conditions were 94° C. for 4 minutes; 94° C. for 2 second and 72° C. for 3 min, 5 cycles; 94° C. for 2 second and 67° C. for 3 minutes, 20 cycles; 67° C. for 3 minutes. Agarose gels were run to determine which PCR gave an optimal fragment length. A 2.1 kb genomic fragment was detected and isolated from the EcoRV-digested genomic DNA reaction. The genomic fragment was digested with BamH I and Sal I and cloned into Bluescript KS$^+$ vector for sequencing. Finally, sequencing data indicated that this genomic fragment contained a 2012 bp soybean annexin promoter sequence as shown in SEQ ID NO:1.

Two gene specific primers (GSP3 and GSP4) were designed for the soybean P34 gene based on the 5' coding sequences in P34 cDNA in NCBI Genebank (J05560). The oligonucleotide sequences of the GSP3 and GSP4 primers have the sequences shown below (SEQ ID NOs:5 and 6).

SEQ ID NO: 5    5'-GGTCCAATATGGAACGATGAGTTGATA-3'

SEQ ID NO: 6    5'-CGC<u>GGATCC</u>GCTGGAACTAGAAGAGAGACC

TAAGA-3'

The AP1 and the GSP3 primers were used in the first round PCR using the same conditions defined in the GenomeWalker™ system protocol. The cycle conditions used for soybean annexin promoter did not work well for the soybean P34 promoter reactions. A modified PCR protocol was used. Cycle conditions were: 94° C. for 4 minutes; 94° C. for 2 second and 74° C. for 3 min, 6 cycles in which annealing temperature drops 1° C. every cycle; 94° C. for 2 second and 69° C. for 3 minutes, 32 cycles; 69° C. for 4 minutes. The products from the 1$^{st}$ run PCR were diluted 50-fold. One microliter of the diluted products were used as templates for the 2$^{nd}$ PCR with the AP2 and GSP4 as primers. Cycle conditions were: 94° C. for 4 minutes; 94° C. for 2 second and 74° C. for 3 min, 6 cycles in which annealing temperature drops 1° C. every cycle; 94° C. for 2 second and 69° C. for 3 minutes, 20 cycles; 69° C. for 3 minutes. A 1.5 kb genomic fragment was amplified and isolated from the Pvu II-digested GenomeWalker library. The genomic fragment was digested with BamH I and Sal I and cloned into Bluescript KS$^+$ vector for sequencing. Sequencing data indicated that this genomic fragment contained a 1408 bp soybean P34 promoter sequence as shown in SEQ ID NO:2.

Example 2

Construction of GUS Reporter Constructs linked to Soybean Annexin Promoter or P34 Promoter and Expression in *Arabidopsis* Seeds Two oligonucleotides were designed to re-amplify the annexin promoter with either BamH I or Nco I sites (underlined below in SEQ ID NOs: 7 and 8, respectively). The oligonucleotide sequences of these two oligonucleotides are shown in SEQ ID NOs:7 and 8.

SEQ ID NO: 7    5'-CGC
                <u>GGATCC</u>ATCTTAGGCCCTTGATTATATGGTG

TTT-3'

SEQ ID NO: 8    5'-CCTTGA
                <u>CCATGG</u>AAGTATTGCTTCTTAGTTAACC

TTTCC-3'

The re-amplified annexin promoter fragment was digested with BamH I and Nco I, purified and cloned into the BamH I and Nco I sites of plasmid pG4G to make the fusion between the soybean annexin promoter-GUS fusion (pJS86). The plasmid pG4G has been described in U.S. Pat. No. 5,968,793 the contents of which are hereby incorporated by reference.

Two oligonucleotides with either BamH I or Nco I sites at the 5' ends were designed to re-amplify the P34 promoter. The oligonucleotide sequences of these two PCR primers are shown in SEQ ID NOs:9 and 10.

SEQ ID NO: 9    5'-CGC<u>GGATCC</u>AACTAAAAAAAGCTCTCAAATTACA

TTTTGAG-3'

SEQ ID NO: 10   5'-CCTTGA<u>CCATGG</u>CTTGGTGGAAGAATTTTATGAT

TTGAAATT-3'.

3'. The re-amplified p34 promoter fragment was digested with BamH I and Nco I, purified and cloned into the BamH I and Nco I sites of plasmid pG4G to make the fusion between the soybean p34 promoter-GUS fusion (pJS87).

The chimeric promoter-GUS recombinant constructs were cloned as a BamH I-Sal I fragment into the *Agrobacterium tumefaciens* binary vector pZBL120 to create pJS90 and pJS91. The binary vector pZBL120 is the same as the pZBL1 binary vector as described in U.S. Pat. No. 5,968,793 (ATCC# 209128) except the NOS promoter was replaced with a 963 bp 35S promoter (NCBI accession number V00141 from nucleotide 6494 to 7456) in the Nos/P-nptII-OCS 3' gene. The new 35S promoter-nptII-OCS 3' gene serves as a kanamycin resistance plant selection marker in pZBL120. The pJS90 and pJS91 binary vector constructions were transformed into *Agrobacterium tumefaciens* LBA4404, which was then used to inoculate *Arabidopsis* plants by Vacuum infiltration (Guang-Ning Ye et. al., *Plant Journal* 19, 249–257,1999). The *Arabidopsis* seeds of primary transformants were selected by 100 mg/l Kan on MS culture plates. The Kan resistant seedlings were transferred into soil and analyzed for GUS activity in seeds, leaves, stems, flowers and silique coats. The GUS activity was analyzed by histochemical staining by X-Gluc and quantitative fluorometric MUG GUS assay as described by Jefferson (*Plant Mol. Biol. Rep.* 5:387–405, 1987).

As shown in FIG. 1 and FIG. 2, both soybean annexin promoter and P34 promoter provide very specific GUS expression in seeds (dark seeds are stained blue in the figures). Other parts of transformed plants, such as leaves, stems, flowers and silique coats, did not exhibit GUS staining (data not shown). The annexin promoter is much stronger than the p34 promoter is for seed specific expression. As shown in FIG. 3, the annexin gene is expressed in a very early stage of seed development, as compared to a mid-late stage gene P34 and other seed storage protein genes.

Example 3

Construction of Annexin Promoter-*M. alpina* Delta-6 Desaturase Constructs and Polyunsaturated Fatty Acid Production in Transgenic Soybean Somatic Embryos Based on the sequences of cloned soybean annexin promoter, another oligo with Not I site at the 5' end was designed and used with BamH I primer (SEQ ID No.7) to re-amplify the annexin promoter. The oligonucleotide sequence of this Not I-containing oligo is shown in SEQ ID No.11.

SEQ ID No. 11: GAATT CGCGGCCGCTGAAGTATTGCTTCTTAGTTAACCTTTCC

Based on the sequences of cloned soybean P34 promoter, another oligo with NotI site at the 5' end was designed and used with BamH I primer (SEQ ID No. 9) to re-amplify the P34 promoter. The oligonucleotide sequence of this NotI-containing oligo is shown in SEQ ID No.12.

SEQ ID No. 12:

GAATTCGCGGCCGCAACTTGGTGGAAGAATTTTATGATTTGAAA

The re-amplified annexin and P34 promoter fragment was digested with BamH I and Not I, purified and cloned into the BamH I and Not I sites of plasmid pZBL115 to make pJS88 and pJS89. The pZBL115 plasmid contains the origin of replication from pRB322, the bacterial HPT hygromycin resistance gene driven by T7 promoter and T7 terminator, and a 35S promoter-HPT-Nos3' gene to serve as a hygromycin resistant plant selection marker. *M. alpina* delta 6 desaturase gene was cloned into Not I site of pJS88 and pJS89 in the sense orientation to make plant expression cassettes pJS92 and pJS93. The pJS92 and pJS93 were transformed into a soybean somatic embryo system. The matured transgenic embryos were analyzed for novel GLA (γ-linolenic acid) production by HPLC/GC.

As shown in FIG. 4, GLA accumulation in soybean somatic embryos was detected when the *M. alpina* delta 6 desaturase gene was under the control of a variety of soybean seed specific promoters. With very strong seed specific promoters such as soybean beta-conglycinin alpha' subunit promoter, soybean Glycinin Gy1 promoter, GLA level is about 35–40%. With soybean annexin promoter, the level of GLA reaches about 40% of total fatty acids. As for soybean P34 promoter, GLA level is about 8%. All these results demonstrated that the soybean annexin and P34 promoters are functional in soybean somatic embryos to produce a novel fatty acid GLA.

Example 4

Identification Seed-Specific Consensus Elements in Annexin and P34 Promoters

The soybean annexin promoter contains the consensus core promoter sequences known as CCAAT box, TATA box and transcription start site. The annexin promoter also contains several seed-specific/ABA responsive elements, such as the RY-G-box seed-specific coupling elements (CATGCAA, CATGCCT, CATGCAG, CTACGTCA, TAACGTGC), ACAC elements (CCTACACTCT, CCAACACTGG, TATACACTCC, TGTACACATA, TTCACACCAT, ACAACACTTT, CTAACACGAT), GTGT elements (ATGGTGTTTA, GTAGTGTGAA, AATGTGTTAT, CATGTGTAAA) and AT-rich sequences. All these conserved elements, individually or in combination, can be very important for the temporal and tissue-specific gene expression of the soybean annexin promoter.

The soybean P34 promoter contains two putative TATA boxes (TATATA and TATATATA). The P34 promoter also contains several seed-specific/ABA responsive elements, such as the RY-G-box seed-specific coupling elements (CATGCAG, CATGCAA, CATGCTA, ACACGTTA, AGACGTGT, GGACGTATACACGTTT, TTACGTAT), ACAC elements (CAACACGT, AAACACACAT, ATACACGT), GTGT elements (GACGTGTACG, GCAGTGTCGA, CATGTGTGAA, ACTGTGTGCT, TTTGTGTTAG). It is interesting to notice that there are two overlapping ACAC element/ACGT elements and one overlapping ACGT element/GTGT element within the promoter, which may play a very important role for both seed-specific and ABA-regulated gene expressions. All these conserved elements, individually or in combination, may be very important for the temporal and tissue-specific gene expression of the soybean P34 promoter.

Example 5

Deletion and Site-directed Mutagenesis of Annexin and P34 Promoters

In order to further define the transcriptional elements controlling temporal and tissue-specific gene expression of these new soybean seed specific promoters, a series of 5' unidirectional deletions of the promoters were made using PCRs. PCRs were also used to make internal deletion and site-directed mutagenesis in the promoters. All these deletion or mutated promoter-GUS constructs were transferred into binary vectors and transformed into transgenic *Arabidopsis* (as described in Example 2).

FIG. 5 shows the ten different deletion fragments that were tested for the annexin promoter (SEQ ID NOs:13–22). The consensus elements identified in Example 4 are shown as boxes. The fragment lengths are 1883 bp, 1719 bp, 1553 bp, 1367 bp, 1160 bp, 967 bp, 770 bp, 584 bp, 425 bp, and 174 bp (SEQ ID NOs:13–22 respectively).

Analysis of the relative promoter strengths and their tissue-specificity of expression was performed by histochemical GUS staining with X-Gluc and quantitative fluorometric MUG GUS assay (as described in Example 2). The results shown in Table 1 and FIG. 6 demonstrate that all of the annexin promoters tested, except the shortest (–174 bp, SEQ ID NO:22), retain high levels of promoter activity.

The –174 promoter may retain some very low level activity. The highest promoter activity is seen with the –770 promoter (SEQ ID NO:19).

TABLE 1

|  | GUS (pmol MU/ug protein · hr) | Standard Deviation |
| --- | --- | --- |
| WT seeds | −0.19173 | 0.55127 |
| −1883 | 1164.2 | 543.89 |
| −1719 | 1418.8 | 606.94 |
| −1553 | 1340.4 | 379.76 |
| −1367 | 913.87 | 434.69 |
| −1160 | 1161.2 | 895.42 |
| −967 | 1407.9 | 760.74 |
| −770 | 2831.7 | 1233.1 |
| −584 | 1388.2 | 760.81 |
| −425 | 519.22 | 221.11 |
| −174 | 0.99894 | 1.9657 |

What is claimed is:

1. An isolated nucleic acid fragment comprising a seed-specific soybean promoter wherein said promoter consists essentially of the nucleotide sequence set forth in any of SEQ ID NO:1 or 13–21.

2. A recombinant expression construct comprising at least one heterologous nucleic acid fragment operably linked to any one of the isolated nucleic acid fragments of claim 1.

3. A plant comprising in its genome the recombinant expression construct of claim 2 wherein said construct is expressed in seed of the plant.

4. The plant of claim 3 wherein said plant is selected from the group consisting of dicotyledonous plants.

5. The plant of claim 4 wherein the plant is soybean.

6. The recombinant expression construct of claim 2 wherein the heterologous nucleic acid fragment encodes an enzyme related to production of at least one long chain polyunsaturated fatty acid.

7. A method for regulating expression of at least one heterologous nucleotide sequence in the seeds of a plant which comprises:
   (a) transforming a plant cell with the recombinant expression construct of claim 2;
   (b) growing fertile mature plants from transformed plant cell of step (a); and
   (c) selecting plants comprising the recombinant expression construct wherein the heterologous nucleotide sequence is expressed in the seeds of the transformed plant.

8. The method of claim 7 wherein the plant is a soybean plant.

9. The method of claim 7 wherein the heterologous nucleic acid fragment encodes an enzyme related to production of at least one long chain polyunsaturated fatty acid.

10. A method for regulating expression of at least one heterologous nucleotide sequence in the seeds of a plant which comprises: (a) transforming a plant cell with a recombinant expression construct comprising at least one heterologous nucleic acid fragment operably linked to the isolated nucleic acid fragment of claim 1 (b) growing fertile mature plants from transformed plant cell of step (a); and (c) selecting plants comprising the recombinant expression construct wherein the heterologous nucleotide sequence is expressed in the seeds of the transformed plant during early seed development.

* * * * *

SEQUENCE LISTING

<160> NUMBER OF SEQ ID NOS: 22

<210> SEQ ID NO 1
<211> LENGTH: 2012
<212> TYPE: DNA
<213> ORGANISM: Glycine max

<400> SEQUENCE: 1

```
atcttaggcc cttgattata tggtgtttag atggattcac atgcaagttt ttatttcaat      60
cccttttcct ttgaataact gaccaagaac aacaagaaaa aaaaaaaaag aaaaggatca     120
ttttgaaagg atattttccg ctcctattca aatactgtat ttttaccaaa aaaactgtat     180
ttttcctaca ctctcaagct ttgttttttcg cttcgactct catgatttcc ttcatatgcc     240
aatcactcta tttataaatg cataaggta gtgtgaacaa ttgcaaagct tgtcatcaaa     300
agcttgcaat gtacaaatta atgttttttca tgcctttcaa aattatctgc accccctagc     360
tattaatcta acatctaagt aaggctagtg aattttttcg aatagtcatg cagtgcatta     420
atttccccgt gactattttg gctttgactc caacactggc cccgtacatc cgtccctcat     480
tacatgaaaa gaaatattgt ttatattctt aattaaaaat attgtccctt ctaaattttc     540
atatagttaa ttattatatt acttttttct ctattctatt agttctattt tcaaattatt     600
atttatgcat atgtaaagta cattatattt ttgctatata cttaaatatt tctaaattat     660
taaaaaaaga ctgatatgaa aaattttattc tttttaaagc tatatcattt tatatatact     720
ttttcttttc ttttcttttca ttttctattc aatttaataa gaaataaatt ttgtaaattt     780
ttatttatca atttataaaa atattttact ttatatgttt tttcacattt ttgttaaaca     840
aatcatatca ttatgattga agagaggaa attgacagtg agtaataagt gatgagaaaa     900
aaatgtgtta tttcctaaaa aaacctaaa caaacatgta tctactctct atttcatcta     960
tctctcattt cattttctc tttatctctt tctttatttt tttatcatat catttcacat    1020
taattatttt tactctcttt attttttctc tctatccctc tcttatttcc actcatatat    1080
acactccaaa attggggcat gcctttatca ctactctatc tcctccacta aatcatttaa    1140
atgaaactga aaagcattgg caagtctcct ccccctcctca agtgatttcc aactcagcat    1200
tggcatctga ttgattcagt atatctattg catgtgtaaa agtctttcca caatacataa    1260
ctattaatta atcttaaata aataaaggat aaaatatttt ttttttcttca taaaattaaa    1320
atatgttatt ttttgtttag atgtatattc gaataaatct aaatatatga taatgatttt    1380
ttatattgat taaacatata atcaatatta aatatgatat ttttttatat aggttgtaca    1440
cataatttta taaggataaa aaatatgata aaaataaatt ttaaatattt ttatatttac    1500
gagaaaaaaa aatattttag ccataaataa atgaccagca tattttacaa ccttagtaat    1560
tcataaattc ctatatgtat atttgaaatt aaaaacagat aatcgttaag ggaaggaatc    1620
ctacgtcatc tcttgccatt tgttttttcat gcaaacagaa agggacgaaa aaccacctca    1680
ccatgaatca ctcttcacac cattttttact agcaaacaag tctcaacaac tgaagccagc    1740
tctcttccccg tttcttttta caacacttttc tttgaaatag tagtatttttt ttttcacatg    1800
atttattaac gtgccaaaag atgcttattg aatagagtgc acatttgtaa tgtactacta    1860
attagaacat gaaaaagcat tgttctaaca cgataatcct gtgaaggcgt taactccaaa    1920
gatccaattt cactatataa aattgtgacga aagcaaaatg aattcacata gctgagagag    1980
aaaggaaagg ttaactaaga agcaatactt ca                                   2012
```

<210> SEQ ID NO 2
<211> LENGTH: 1408
<212> TYPE: DNA
<213> ORGANISM: Glycine max

<400> SEQUENCE: 2

```
aactaaaaaa agctctcaaa ttacattttg agttgtttca ggttccattg ccttattgct      60
aaaactccaa ctaaaataac aaatagcaca tgcaggtgca acaacacgt tactctgatg      120
aaggtgatgt gcctctagca gtctagctta tgaggctcgc tgcttatcaa cgattcatca     180
ttccccaaga cgtgtacgca gattaaacaa tggacaaaac ttcaatcgat tatagaataa     240
taattttaac agtgccgact tttttctgta aacaaaaggc cagaatcata tcgcacatca     300
tcttgaatgc agtgtcgagt ttggaccatt tgagtacaaa gccaatattg aatgattttt     360
cgattttaca tgtgtgaatc agacaaaagt gcatgcaatc acttgcaagt aaattaagga     420
tactaatcta ttcctttcat tttatatgct ccacttttat ataaaaaaat atacattatt     480
atatatgcat tattaattat tgcagtatta tgctattggt tttatggccc tgctaaataa     540
cctaaatgag tctaactatt gcatatgaat caaatgaagg aagaatcatg atctaaacct     600
gagtacccaa tgcaataaaa tgcgtcctat tacctaaact tcaaacacac attgccatcg     660
gacgtataaa ttaatgcata taggttattt tgagaaaaga aaacatcaaa agctctaaaa     720
cttcttttaa ctttgaaata agctgataaa aatacgcttt aaatcaactg tgtgctgtat     780
ataagctgca atttcacatt ttaccaaacc gaaacaagaa tggtaacagt gaggcaaaaa     840
tttgaaaaat gtcctacttc acattcacat caaattaatt acaactaaat aaataaacat     900
cgtgattcaa gcagtaatga aagtcgaaat cagatagaat atacacgttt aacatcaatt     960
gaatttttt ttaaatggat atatacaagt ttactatttt atatataatg aaaattcatt     1020
ttgtgttagc acaaaactta cagaaagaga taaattttaa ataaagagaa ttatatccaa    1080
ttttataatc caaataatc aaattaaaga atattggcta gatagaccgg cttttcact     1140
gccctgctg gataatgaaa attcatatca aaacaataca gaagttctag tttaataata     1200
aaaagttgg caaactgtca ttccctgttg gttttaagc caaatcacaa ttcaattacg     1260
tatcagaaat taatttaaac caaatatata gctacgaggg aacttcttca gtcattacta    1320
gctagctcac taatcactat atatacgaca tgctacaagt gaagtgacca tatcttaatt    1380
tcaaatcata aaattcttcc accaagtt                                        1408
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 3

```
gccccccatc ctttgaaagc ctgt                                             24
```

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 4

```
cgcggatccg agagcctcag catcttgagc agaa                              34
```

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 5

```
ggtccaatat ggaacgatga gttgata                                      27
```

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: PCR primer

<400> SEQUENCE: 6

```
cgcggatccg ctggaactag aagagagacc taaga                             35
```

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: PCR primer

<400> SEQUENCE: 7

```
cgcggatcca tcttaggccc ttgattatat ggtgttt                           37
```

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: PCR primer

<400> SEQUENCE: 8

```
ccttgaccat ggaagtattg cttcttagtt aacctttcc                         39
```

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: PCR primer

<400> SEQUENCE: 9

```
cgcggatcca actaaaaaaa gctctcaaat tacattttga g                      41
```

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: PCR primer

<400> SEQUENCE: 10

```
ccttgaccat ggcttggtgg aagaatttta tgatttgaaa tt                     42
```

<210> SEQ ID NO 11
<211> LENGTH: 43
<212> TYPE: DNA
<213> ORGANISM: Artificial Sequence -continued

```
<220> FEATURE:
<223> OTHER INFORMATION: Description of Artificial Sequence: PCR primer

<400> SEQUENCE: 11
gaattcgcgg ccgctgaagt attgcttctt agttaacctt tcc                    43

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: PCR primer

<400> SEQUENCE: 12
gaattcgcgg ccgcaacttg gtggaagaat tttatgattt gaaa                   44

<210> SEQ ID NO 13
<211> LENGTH: 1883
<212> TYPE: DNA
<213> ORGANISM: Glycine max

<400> SEQUENCE: 13 gatattttc gctcctattc aaatactgta ttttaccaa aaaaactgta tttttcctac     60
actctcaagc tttgttttc gcttcgactc tcatgattc cttcatatgc caatcactct   120
atttataaat ggcataaggt agtgtgaaca attgcaaagc ttgtcatcaa aagcttgcaa   180
tgtacaaatt aatgtttttc atgcctttca aaattatctg cacccctag ctattaatct   240 aacatctaag taaggctagt gaatttttc gaatagtcat gcagtgcatt aatttccccg   300
tgactatttt ggctttgact ccaacactgg ccccgtacat ccgtccctca ttacatgaaa   360
agaaatattg tttatattct taattaaaaa tattgtccct tctaaatttt catatagtta   420
attattatat actttttc tctattctat tagttctatt ttcaaattat tatttatgca   480
tatgtaaagt acattatatt tttgctatat acttaaatat ttctaaatta ttaaaaaaag   540
actgatatga aaatttatt cttttttaaag ctatatcatt ttatatatac ttttctttt   600 cttttcttc attttctatt caatttaata agaaataaat tttgtaaatt tttattatc   660 aatttataaa aatattttac tttatatgtt tttcacatt tttgttaaac aaatcatatc   720
attatgattg aaagagagga aattgacagt gagtaataag tgatgagaaa aaaatgtgtt   780
atttcctaaa aaaaacctaa acaaacatgt atctactctc tatttcatct atctctcatt   840 tcattttct cttatctct ttctttattt ttttatcata tcatttcaca ttaattattt   900
ttactctctt tatttttct ctctatccct ctcttatttc cactcatata tacactccaa   960
aattggggca tgcctttatc actactctat ctcctccact aaatcattta aatgaaactg  1020
aaaagcattg gcaagtctcc tccccctcctc aagtgatttc caactcagca ttggcatctg  1080
attgattcag tatatctatt gcatgtgtaa agtctttcc acaatacata actattaatt  1140
aatcttaaat aaataaagga taaatatttt ttttttcttc ataaaattaa aatatgttat  1200
tttttgttta gatgtatatt cgaataaatc taaatatatg ataatgattt tttatattga  1260
ttaaacatat aatcaatatt aaatatgata tttttttata taggttgtac acataatttt  1320
ataaggataa aaaatatgat aaaaataaat tttaaatatt tttatattta cgagaaaaaa  1380
aaatatttta gccataaata aatgaccagc atatttaca accttagtaa ttcataaatt  1440
cctatatgta tatttgaaat taaaacaga taatcgttaa gggaaggaat cctacgtcat  1500
ctcttgccat ttgttttca tgcaaacaga aagggacgaa aaaccacctc accatgaatc  1560
```

-continued

| | |
|---|---|
| actcttcaca ccatttttac tagcaaacaa gtctcaacaa ctgaagccag ctctcttttcc | 1620 |
| gtttctttttt acaacacttt ctttgaaata gtagtatttt tttttcacat gatttattaa | 1680 |
| cgtgccaaaa gatgcttatt gaatagagtg cacatttgta atgtactact aattagaaca | 1740 |
| tgaaaaagca ttgttctaac acgataatcc tgtgaaggcg ttaactccaa agatccaatt | 1800 |
| tcactatata aattgtgacg aaagcaaaat gaattcacat agctgagaga gaaaggaaag | 1860 |
| gttaactaag aagcaatact tca | 1883 |

<210> SEQ ID NO 14
<211> LENGTH: 1719
<212> TYPE: DNA
<213> ORGANISM: Glycine max

<400> SEQUENCE: 14

| | |
|---|---|
| catcaaaagc ttgcaatgta caaattaatg ttttttcatgc ctttcaaaat tatctgcacc | 60 |
| ccctagctat taatctaaca tctaagtaag gctagtgaat ttttttcgaat agtcatgcag | 120 |
| tgcattaatt tccccgtgac tattttggct ttgactccaa cactggcccc gtacatccgt | 180 |
| ccctcattac atgaaaagaa atattgttta tattcttaat taaaaatatt gtcccttcta | 240 |
| aattttcata tagttaatta ttatattact tttttctcta ttctattagt tctatttttca | 300 |
| aattattatt tatgcatatg taaagtacat tatatttttg ctatatactt aaatattttct | 360 |
| aaattattaa aaaagactg atatgaaaaa tttattcttt ttaaagctat atcattttat | 420 |
| atatactttt tctttttcttt tctttcattt tctattcaat ttaataagaa ataaattttg | 480 |
| taaattttta tttatcaatt tataaaaata ttttacttta tatgtttttt cacattttg | 540 |
| ttaaacaaat catatcatta tgattgaaag agaggaaatt gacagtgagt aataagtgat | 600 |
| gagaaaaaaa tgtgttattt cctaaaaaaa acctaaacaa acatgtatct actctctatt | 660 |
| tcatctatct ctcatttcat ttttctcttt atctctttct ttattttttt atcatatcat | 720 |
| ttcacattaa ttattttttac tctctttatt ttttctctct atccctctct tatttccact | 780 |
| catatataca ctccaaaatt ggggcatgcc tttatcacta ctctatctcc tccactaaat | 840 |
| catttaaatg aaactgaaaa gcattggcaa gtctcctccc ctcctcaagt gatttccaac | 900 |
| tcagcattgg catctgattg attcagtata tctattgcat gtgtaaaagt ctttccacaa | 960 |
| tacataacta ttaattaatc ttaaataaat aaaggataaa atatttttt ttcttcataa | 1020 |
| aattaaaata tgttatttttt tgtttagatg tatattcgaa taaatctaaa tatatgataa | 1080 |
| tgattttttta tattgattaa acatataatc aatattaaat atgatatttt tttatatagg | 1140 |
| ttgtacacat aatttttataa ggataaaaaa tatgataaaa ataaatttta aatattttta | 1200 |
| tatttacgag aaaaaaaaat attttagcca taaataaatg accagcatat tttacaacct | 1260 |
| tagtaattca taaattccta tatgtatatt tgaaattaaa aacagataat cgttaaggga | 1320 |
| aggaatccta cgtcatctct tgccatttgt ttttcatgca aacagaaagg gacgaaaaac | 1380 |
| cacctcacca tgaatcactc ttcacaccat ttttactagc aaacaagtct caacaactga | 1440 |
| agccagctct ctttccgttt cttttttacaa cactttctttt gaatagtag tatttttttt | 1500 |
| tcacatgatt tattaacgtg ccaaagatg cttattgaat agagtgcaca tttgtaatgt | 1560 |
| actactaatt agaacatgaa aaagcattgt tctaacacga taatcctgtg aaggcgttaa | 1620 |
| ctccaaagat ccaatttcac tatataaatt gtgacgaaag caaatgaat tcacatagct | 1680 |
| gagagagaaa ggaaaggtta actaagaagc aatacttca | 1719 |

<210> SEQ ID NO 15
<211> LENGTH: 1553
<212> TYPE: DNA
<213> ORGANISM: Glycine max

<400> SEQUENCE: 15

| | | | | | |
|---|---|---|---|---|---|
| ccccgtacat | ccgtccctca | ttacatgaaa | agaaatattg | tttatattct | taattaaaaa | 60 |
| tattgtccct | tctaaatttt | catatagtta | attattatat | tacttttttc | tctattctat | 120 |
| tagttctatt | ttcaaattat | tatttatgca | tatgtaaagt | acattatatt | tttgctatat | 180 |
| acttaaatat | ttctaaatta | ttaaaaaaag | actgatatga | aaaatttatt | cttttttaaag | 240 |
| ctatatcatt | ttatatatac | ttttttcttt | cttttctttc | attttctatt | caatttaata | 300 |
| agaaataaat | tttgtaaatt | tttatttatc | aatttataaa | aatattttac | tttatatgtt | 360 |
| ttttcacatt | tttgttaaac | aaatcatatc | attatgattg | aaagagagga | aattgacagt | 420 |
| gagtaataag | tgatgagaaa | aaaatgtgtt | atttcctaaa | aaaaacctaa | acaaacatgt | 480 |
| atctactctc | tatttcatct | atctctcatt | tcattttct | ctttatctct | ttctttattt | 540 |
| ttttatcata | tcatttcaca | ttaattattt | ttactctctt | tattttttct | ctctatccct | 600 |
| ctcttatttc | cactcatata | tacactccaa | aatttggggca | tgcctttatc | actactctat | 660 |
| ctcctccact | aaatcattta | aatgaaactg | aaaagcattg | gcaagtctcc | tcccctcctc | 720 |
| aagtgatttc | caactcagca | ttggcatctg | attgattcag | tatatctatt | gcatgtgtaa | 780 |
| aagtctttcc | acaatacata | actattaatt | aatcttaaat | aaataaagga | taaatatttt | 840 |
| ttttttcttc | ataaaattaa | aatatgttat | tttttgttta | gatgtatatt | cgaataaatc | 900 |
| taaatatatg | ataatgattt | tttatattga | ttaaacatat | aatcaatatt | aaatatgata | 960 |
| ttttttttata | taggttgtac | acataatttt | ataaggataa | aaaatatgat | aaaaataaat | 1020 |
| tttaaatatt | tttatattta | cgagaaaaaa | aaatatttta | gccataaata | aatgaccagc | 1080 |
| atatttaca | accttagtaa | ttcataaatt | cctatatgta | tatttgaaat | taaaaacaga | 1140 |
| taatcgttaa | gggaaggaat | cctacgtcat | ctcttgccat | ttgttttttca | tgcaaacaga | 1200 |
| aagggacgaa | aaaccacctc | accatgaatc | actcttcaca | ccattttac | tagcaaacaa | 1260 |
| gtctcaacaa | ctgaagccag | ctctctttcc | gtttcttttt | acaacacttt | ctttgaaata | 1320 |
| gtagtatttt | ttttttcacat | gatttattaa | cgtgccaaaa | gatgcttatt | gaatagagtg | 1380 |
| cacatttgta | atgtactact | aattagaaca | tgaaaaagca | ttgttctaac | acgataatcc | 1440 |
| tgtgaaggcg | ttaactccaa | agatccaatt | tcactatata | aattgtgacg | aaagcaaaat | 1500 |
| gaattcacat | agctgagaga | gaaaggaaag | gttaactaag | aagcaatact | tca | 1553 |

<210> SEQ ID NO 16
<211> LENGTH: 1367
<212> TYPE: DNA
<213> ORGANISM: Glycine max

<400> SEQUENCE: 16

| | | | | | |
|---|---|---|---|---|---|
| atatttctaa | attattaaaa | aaagactgat | atgaaaaatt | tattcttttt | aaagctatat | 60 |
| cattttatat | atacttttttc | ttttcttttc | tttcattttc | tattcaattt | aataagaaat | 120 |
| aaatttgta | aattttttatt | tatcaattta | taaaaatatt | ttactttata | tgttttttca | 180 |
| cattttgtt | aaacaaatca | tatcattatg | attgaaagag | aggaaattga | cagtgagtaa | 240 |
| taagtgatga | gaaaaaaatg | tgttatttcc | taaaaaaaac | ctaaacaaac | atgtatctac | 300 |
| tctctatttc | atctatctct | catttcattt | ttctctttat | ctctttcttt | atttttttat | 360 |

-continued

| | |
|---|---|
| catatcattt cacattaatt attttttactc tctttatttt ttctctctat ccctctctta | 420 |
| tttccactca tatatacact ccaaaattgg ggcatgcctt tatcactact ctatctcctc | 480 |
| cactaaatca tttaaatgaa actgaaaagc attggcaagt ctcctcccct cctcaagtga | 540 |
| tttccaactc agcattggca tctgattgat tcagtatatc tattgcatgt gtaaaagtct | 600 |
| ttccacaata cataactatt aattaatctt aaataaataa aggataaaat atttttttt | 660 |
| cttcataaaa ttaaaatatg ttatttttg tttagatgta tattcgaata aatctaaata | 720 |
| tatgataatg atttttata ttgattaaac ataatcaa tattaaatat gatattttt | 780 |
| tataggtt gtacacataa ttttataagg ataaaaata tgataaaat aaattttaaa | 840 |
| tattttata tttacgagaa aaaaaatat tttagccata aataaatgac cagcatattt | 900 |
| tacaaccta gtaattcata aattcctata tgtatatttg aaattaaaaa cagataatcg | 960 |
| ttaagggaag gaatcctacg tcatctcttg ccatttgttt tcatgcaaa cagaaaggga | 1020 |
| cgaaaaacca cctcaccatg aatcactctt cacaccattt ttactagcaa caagtctca | 1080 |
| acaactgaag ccagctctct ttccgtttct ttttacaaca cttctttga aatagtagta | 1140 |
| ttttttttc acatgattta ttaacgtgcc aaaagatgct tattgaatag agtgcacatt | 1200 |
| tgtaatgtac tactaattag aacatgaaaa agcattgttc taacacgata atcctgtgaa | 1260 |
| ggcgttaact ccaaagatcc aatttcacta tataaattgt gacgaaagca aaatgaattc | 1320 |
| acatagctga gagagaaagg aaaggttaac taagaagcaa tacttca | 1367 |

<210> SEQ ID NO 17
<211> LENGTH: 1160
<212> TYPE: DNA
<213> ORGANISM: Glycine max

<400> SEQUENCE: 17

| | |
|---|---|
| atgattgaaa gagaggaaat tgacagtgag taataagtga tgagaaaaaa atgtgttatt | 60 |
| tcctaaaaaa aacctaaaca aacatgtatc tactctctat ttcatctatc tctcatttca | 120 |
| ttttctctt tatctctttc tttatttttt tatcatatca tttcacatta attatttta | 180 |
| ctctctttat tttttctctc tatccctctc ttatttccac tcatatatac actccaaaat | 240 |
| tggggcatgc ctttatcact actctatctc ctccactaaa tcatttaaat gaaactgaaa | 300 |
| agcattggca agtctcctcc cctcctcaag tgatttccaa ctcagcattg gcatctgatt | 360 |
| gattcagtat atctattgca tgtgtaaaag tcttttccaca atacataact attaattaat | 420 |
| cttaaataaa taaaggataa atatttttt tttcttcata aaattaaaat atgttattt | 480 |
| ttgtttagat gtatattcga ataaatctaa atatatgata atgattttt atattgatta | 540 |
| aacatataat caatattaaa tatgatattt ttttatatag gttgtacaca taattttata | 600 |
| aggataaaaa atatgataaa aataaatttt aaatatttt atatttacga gaaaaaaaaa | 660 |
| tattttagcc ataaataaat gaccagcata ttttacaacc ttagtaattc ataaattcct | 720 |
| atatgtatat ttgaaattaa aaacagataa tcgttaaggg aaggaatcct acgtcatctc | 780 |
| ttgccatttg ttttcatgc aaacagaaag ggacgaaaaa ccacctcacc atgaatcact | 840 |
| cttcacacca tttttactag caaacaagtc tcaacaactg aagccagctc tctttccgtt | 900 |
| tctttttaca acactttctt tgaaatagta gtatttttt ttcacatgat ttattaacgt | 960 |
| gccaaaagat gcttattgaa tagagtgcac atttgtaatg tactactaat tagaacatga | 1020 |
| aaaagcattg ttctaacacg ataatcctgt gaaggcgtta actccaaaga tccaatttca | 1080 |
| ctatataaat tgtgacgaaa gcaaaatgaa ttcacatagc tgagagagaa aggaaaggtt | 1140 |

```
aactaagaag caatacttca                                              1160

<210> SEQ ID NO 18
<211> LENGTH: 967
<212> TYPE: DNA
<213> ORGANISM: Glycine max

<400> SEQUENCE: 18
ttctctctat ccctctctta tttccactca tatatacact ccaaaattgg ggcatgcctt      60
tatcactact ctatctcctc cactaaatca tttaaatgaa actgaaaagc attggcaagt     120
ctcctcccct cctcaagtga tttccaactc agcattggca tctgattgat tcagtatatc     180
tattgcatgt gtaaaagtct tccacaata cataactatt aattaatctt aaataaataa      240
aggataaaat attttttttt cttcataaaa ttaaaatatg ttattttttg tttagatgta     300
tattcgaata aatctaaata tatgataatg attttttata ttgattaaac atataatcaa     360
tattaaatat gatatttttt tatataggtt gtacacataa ttttataagg ataaaaata      420 tgataaaaat aaattttaaa tattttata tttacgagaa aaaaaatat tttagccata       480 aataaatgac cagcatattt tacaaccta gtaattcata aattcctata tgtatatttg      540
aaattaaaaa cagataatcg ttaagggaag gaatcctacg tcatctcttg ccatttgttt     600
ttcatgcaaa cagaaaggga cgaaaaacca cctcaccatg aatcactctt cacaccattt     660
ttactagcaa acaagtctca caactgaag ccagctctct ttccgtttct ttttacaaca      720
ctttctttga aatagtagta ttttttttc acatgattta ttaacgtgcc aaaagatgct     780
tattgaatag agtgcacatt tgtaatgtac tactaattag aacatgaaaa agcattgttc     840
taacacgata atcctgtgaa ggcgttaact ccaaagatcc aatttcacta tataaattgt     900
gacgaaagca aaatgaattc acatagctga gagagaaagg aaaggttaac taagaagcaa     960
tacttca                                                              967

<210> SEQ ID NO 19
<211> LENGTH: 770
<212> TYPE: DNA
<213> ORGANISM: Glycine max

<400> SEQUENCE: 19
tctttccaca atacataact attaattaat cttaaataaa taaggataaa atattttttt     60
tttcttcata aaattaaaat atgttatttt ttgtttagat gtatattcga ataaatctaa     120
atatatgata atgattttt atattgatta acatataat caatattaaa tatgatatt       180 ttttatatag gttgtacaca taattttata aggataaaaa atatgataaa aataaatttt     240 aaatatttt atatttacga gaaaaaaaaa tattttagcc ataaataaat gaccagcata     300
ttttacaacc ttagtaattc ataaattcct atatgtatat ttgaaattaa aaacagataa     360
tcgttaaggg aaggaatcct acgtcatctc ttgccatttg ttttcatgc aaacagaaag     420 ggacgaaaaa ccacctcacc atgaatcact cttcacacca tttttactag caaacaagtc     480
tcaacaactg aagccagctc tctttccgtt tcttttaca acactttctt tgaaatagta     540
gtattttttt ttcacatgat ttattaacgt gccaaaagat gcttattgaa tagagtgcac     600
atttgtaatg tactactaat tagaacatga aaagcattg ttctaacacg ataatcctgt      660
gaaggcgtta actccaaaga tccaatttca ctatataaat tgtgacgaaa gcaaatgaa     720 ttcacatagc tgagagagaa aggaaaggtt aactaagaag caatacttca                770
```

<210> SEQ ID NO 20
<211> LENGTH: 584
<212> TYPE: DNA
<213> ORGANISM: Glycine max

<400> SEQUENCE: 20

| | | |
|---|---|---|
| ataggttgta cacataattt tataaggata aaaaatatga taaaaataaa ttttaaatat | 60 |
| ttttatattt acgagaaaaa aaaatatttt agccataaat aaatgaccag catattttac | 120 |
| aaccttagta attcataaat tcctatatgt atatttgaaa ttaaaaacag ataatcgtta | 180 |
| agggaaggaa tcctacgtca tctcttgcca tttgttttc atgcaaacag aaagggacga | 240 |
| aaaaccacct caccatgaat cactcttcac accatttta ctagcaaaca agtctcaaca | 300 |
| actgaagcca gctctctttc cgtttctttt tacaacactt tctttgaaat agtagtattt | 360 |
| tttttttcaca tgatttatta acgtgccaaa agatgcttat tgaatagagt gcacatttgt | 420 |
| aatgtactac taattagaac atgaaaaagc attgttctaa cacgataatc ctgtgaaggc | 480 |
| gttaactcca aagatccaat ttcactatat aaattgtgac gaaagcaaaa tgaattcaca | 540 |
| tagctgagag agaaaggaaa ggttaactaa gaagcaatac ttca | 584 |

<210> SEQ ID NO 21
<211> LENGTH: 425
<212> TYPE: DNA
<213> ORGANISM: Glycine max

<400> SEQUENCE: 21

| | | |
|---|---|---|
| attaaaaaca gataatcgtt aagggaagga atcctacgtc atctcttgcc atttgttttt | 60 |
| catgcaaaca gaaagggacg aaaaaccacc tcaccatgaa tcactcttca caccattttt | 120 |
| actagcaaac aagtctcaac aactgaagcc agctctcttt ccgtttcttt ttacaacact | 180 |
| ttctttgaaa tagtagtatt ttttttttcac atgatttatt aacgtgccaa aagatgctta | 240 |
| ttgaatagag tgcacatttg taatgtacta ctaattagaa catgaaaaag cattgttcta | 300 |
| acacgataat cctgtgaagg cgttaactcc aaagatccaa tttcactata taaattgtga | 360 |
| cgaaagcaaa atgaattcac atagctgaga gagaaaggaa aggttaacta agaagcaata | 420 |
| cttca | 425 |

<210> SEQ ID NO 22
<211> LENGTH: 174
<212> TYPE: DNA
<213> ORGANISM: Glycine max

<400> SEQUENCE: 22

| | | |
|---|---|---|
| gcacatttgt aatgtactac taattagaac atgaaaaagc attgttctaa cacgataatc | 60 |
| ctgtgaaggc gttaactcca aagatccaat ttcactatat aaattgtgac gaaagcaaaa | 120 |
| tgaattcaca tagctgagag agaaaggaaa ggttaactaa gaagcaatac ttca | 174 |